United States Patent
Gianchandani et al.

(10) Patent No.: US 7,142,303 B2
(45) Date of Patent: Nov. 28, 2006

(54) MICRO-DISCHARGE OPTICAL SOURCE APPARATUS AND METHOD AND SYSTEM FOR ANALYZING A SAMPLE

(75) Inventors: Yogesh B. Gianchandani, Ann Arbor, MI (US); Ghester G. Wilson, Ruston, LA (US); Long Que, Ann Arbor, MI (US); Bhaskar Mitra, Ann Arbor, MI (US); Ponnambalam Selvaganapathy, Chennai (IN)

(73) Assignee: The Regents of the University of Michigan, Ann Arbor, MI (US)

( * ) Notice: Subject to any disclaimer, the term of this patent is extended or adjusted under 35 U.S.C. 154(b) by 266 days.

(21) Appl. No.: 10/937,918

(22) Filed: Sep. 10, 2004

(65) Prior Publication Data

US 2005/0093417 A1 May 5, 2005

Related U.S. Application Data

(60) Provisional application No. 60/502,445, filed on Sep. 12, 2003.

(51) Int. Cl.
  *G01J 3/10* (2006.01)
  *G01N 21/64* (2006.01)

(52) U.S. Cl. .................. 356/417; 356/317; 250/458.1; 250/461.1; 313/163

(58) Field of Classification Search ............... 356/311, 356/313, 316, 317, 417; 313/163, 165, 619; 250/458.1, 461.1
See application file for complete search history.

(56) References Cited

U.S. PATENT DOCUMENTS 6,686,998 B1 2/2004 Gianchandani et al.

OTHER PUBLICATIONS

Zhu, H., et al., High-Sensitivity Capillary Electrophoresis of Double-Stranded DNA Fragments Using Monomeric and Dimeric Fluorescent Intercalating Dyes, Analytical Chemistry, 66, pp. 1941-8, 1994.

Ladokhin, A.S., Fluorescence Spectroscopy in Peptide and Protein Analysis, Encyclopedia of Analytical Chemistry, Ed. R.A. Meyers, John Wiley & Sons Ltd., 2000, pp. 1-18.

Fasman, G.D., Handbook of Biochemistry and Molecular Biology, Proteins I, CRC Press, 1976, pp. 184-193 and 200-203.

(Continued)

*Primary Examiner*—F. L. Evans
(74) *Attorney, Agent, or Firm*—Brooks Kushman P.C.

(57) ABSTRACT

A micro-discharge optical source apparatus and a method and system which utilizes the apparatus to analyze a sample are provided. The apparatus includes a substrate and an anode electrode and a cathode electrode supported on the substrate. One of the electrodes, such as the cathode, is preferably a liquid electrode. The electrodes are spaced apart to define an inter-electrode gap therebetween. The apparatus further includes a voltage source for applying a voltage between the electrodes sufficient to generate a glow micro-discharge in the gap to cause a first emission having a first desired excitation spectrum. An optical element is integrated with the substrate to direct the first emission to travel along an optical path including an axis. In one embodiment, the system detects the direct fluorescence of a sample such as tryptophan and other amino acids. In another embodiment, the system detects fluorescence of dye-labeled biochemicals.

101 Claims, 5 Drawing Sheets

OTHER PUBLICATIONS

Chen, R., Measurements of Absolute Values in Biochemical Fluorescence Spectroscopy, J. Research National Bureau Standards, 76A(6), 1972, pp. 593-606.

Chou, H., et al., A Microfabricated Device for Sizing & Sorting DNA Molecules, Proc. Natl. Acad. Sci., 96, pp. 11-13, 1999.

Webster, J., et al., Monolithic Capillary Electrophoresis Device With Integrated Fluorescence Detector, Anal. Chem., 73, pp. 1622-1626, 2001.

M. Warren et al., Integrated Micro-optical Fluorescence Detection System for Microfluidic Electro-Chromatography, Proc. SPIE, v. 3878, pp. 185-192, 1999.

Thrush, E., et al., Integrated Semiconductor Fluorescent Detection System for Biochip & Biomedical Applications, Proc. SPIE, 4626, pp. 289-296, 2002.

Que, L., et al., A Water Spectroscopy Microsystem with Integrated Discharge Source, Dispersion Optics, and Sample Delivery, Proc., IEEE Transducers Conf., Boston, Jun. 2003.

Que, L., et al., Dye-Fluorescence LEd-SpEC: A Battery-Operated, On-Chip, Wavelength-Tunable Optical Source for Detection of Biochemicals, Proc. of the Micro Total Analysis Systems Symposium, Squaw Vally, CA, Oct. 2003.

L-Tryptophan, CAS No. 73-22-3, Fischer Scientific, Catalog No. BP395-100, Lot No. 018929.

Light, L.H., et al., Transistor D.C. Convertors, Proc. of IEEE, B, 102, pp. 775-786, 1955.

MICRO-DISCHARGE OPTICAL SOURCE APPARATUS AND METHOD AND SYSTEM FOR ANALYZING A SAMPLE

CROSS-REFERENCE TO RELATED APPLICATION

This application claims the benefit of U.S. provisional application Ser. No. 60/502,445, filed Sep. 12, 2003 and entitled "Battery-Operated Wavelength Tunable Optical Source for Fluorescent Detection of Bio-Chemicals."

STATEMENT REGARDING FEDERALLY SPONSORED RESEARCH OR DEVELOPMENT

This invention was made with partial Government support under Contract No. F30602-00-1-0571 with the Air Force and under Contract No. ECS 0233174 with the National Science Foundation. The Government has certain rights to the invention.

BACKGROUND OF THE INVENTION

1. Field of the Invention

This invention relates to micro-discharge optical source apparatus and methods and systems for analyzing a sample.

2. Background Art

The following references are referenced herein:

[1] H. Zhu et al., "High-Sensitivity Capillary Electrophoresis of Double-Stranded DNA Fragments Using Monomeric and Dimeric Fluorescent Intercalating Dyes," ANALYTICAL CHEMISTRY, 66, pp. 1941–8, 1994.

[2] R. P. Haugland, HANDBOOK OF FLUORESCENCE PROBES AND RESEARCH CHEMICALS, Molecular Probes, Eugene, OR, 1996.

[3] S. V. Konev, FLUORESCENCE AND PHOSPHORESCENCE OF PROTEINS AND NUCLEIC ACIDS, Plenum Press, 1967.

[4] A. S. Ladokhin, "Fluorescence Spectroscopy in Peptide and Protein Analysis," ENCYCLOPEDIA OF ANALYTICAL CHEMISTRY, Ed. R. A. Meyers, John Wiley & Sons Ltd., 2000, pp. 5762–5779.

[5] G. D. Fasman, HANDBOOK OF BIOCHEMISTRY AND MOLECULAR BIOLOGY, PROTEINS I, CRC Press, 1976, pp. 183–203.

[6] R. Chen, "Measurements of Absolute Values in Biochemical Fluorescence Spectroscopy," J. RESEARCH NATIONAL BUREAU STANDARDS, 76A(6), 1972, pp. 593–606.

[7] H. Chou et al., "A Microfabricated Device for Sizing & Sorting DNA Molecules," PROC. NATL. ACAD. SCI., 96, pp. 11–13, 1999.

[8] J. Webster et al., "Monolithic Capillary Electrophoresis Device With Integrated Fluorescence Detector," ANAL. CHEM., 73, pp. 1622–6, 2001.

[9] M. Warren et al., "Integrated Micro-optical Fluorescence Detection System for Microfluidic Electro-Chromatography," PROC. SPIE, v. 3878, pp. 185–192, 1999.

[10] E. Thrush et al., "Integrated Semiconductor Fluorescent Detection System for Biochip & Biomedical Applications," PROC. SPIE, 4626, pp. 289–96, 2002.

[11] L. Que et al., "A Water Spectroscopy Microsystem with Integrated Discharge Source, Dispersion Optics, and Sample Delivery," PROC., IEEE TRANSDUCERS CONF., Boston, June 2003.

[12] L. Que et al., "Dye-Fluorescence LEd-SpEC: A Battery-Operated, On-Chip, Wavelength-Tunable Optical Source for Detection of Biochemicals," PROC. OF THE MICRO TOTAL ANALYSIS SYSTEMS SYMPOSIUM, Squaw Vally, Calif., October 2003.

[13] L-Tryptophan, CAS Number 73-22-3, Fischer Scientific, Catalog Number, BP395-100, Lot Number 018929.

[14] Model number K30-635 and K43-456, Edmund Industrial Optics, Inc., Barrington, N.J.

[15] L. H. Light et al., "Transistor D.C. Convertors," PROC. OF IEEE, B, 102, pp. 775–786, 1955.

Fluorescence detection is a widely used technique for medical diagnostics and biochemical analysis. The molecules of interest fluoresce at characteristic emission wavelengths when they are illuminated at characteristic excitation wavelengths, which are shorter (and hence more energetic).

In one diagnostic approach, a fluorescent dye is used to chemically label the quantity of interest. For DNA detection, dyes which intercalate into the double-helix provide very high sensitivity and make it possible to detect attomoles of DNA base-pairs [1]. A contributing factor to high sensitivity is quantum efficiency, which is the ratio of the number of photons emitted to those absorbed in the excitation wavelengths. For example, SYBR Green I gel stain is a cyanine dye that has a quantum efficiency of 0.8 [2]. When bound to dsDNA, it is most efficiently excited by radiation over 491–503 nm, and has a broad emission spectrum over 510–600 nm, with a peak at 522 nm.

Figure 1:
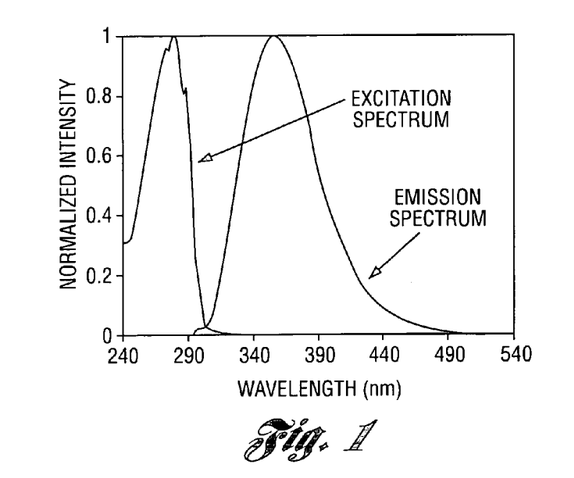
FIG. 1 are graphs of typical excitation and emission spectra of tryptophan which show that the UV source must operate over 250–290 nm wavelengths, whereas the fluorescence peaks over 330–390 nm [5,6]

While dyes offer many attractive features, their use is not always favored or even possible. For example, proteins can be fluorescent even without the presence of a dye, and changes in this intrinsic or direct fluorescence can be indicative of structural transformations [3,4]. The intrinsic fluorescence of proteins and peptides is due to the presence of tryptophan, tyrosine or phenylalanine, which are amino acids. In contrast to the excitation and emission wavelengths for the SYBR green dye, which are in the visible portion of the spectrum, these three have absorption peaks over 250–290 nm and emission peaks over 280–350 nm, all in the deep ultra-violet (UV) region. The characteristics for tryptophan are shown in FIG. 1 [5,6]. (Note that the wavelength at which this fluorescence peaks is highly sensitive to the microenvironment, and hence it is widely used for studying protein structure and dynamics). It is noteworthy that the quantum efficiencies of these amino acids are relatively low. For example, tryptophan, which tends to dominate in fluorescence over the other two, has a quantum efficiency of only 0.19 when dissolved in water as a free amino acid [3]. These characteristic can make it relatively challenging to observe direct fluorescence.

In a typical fluorescence imaging system, the radiation source is often broad-band, so a low-pass filter is located between the source and the sample to reduce its illumination by the longer wavelengths. In addition, a high-pass filter located between the sample and the detector so as to restrict the measured signal to the fluorescence wavelengths and minimize the radiation from the source that might inadvertently leak through.

In recent years, significant research has been devoted to miniaturization of biochemical instrumentation, leading to micro-total analysis systems (also referred to as "lab-on-a-chip"). With respect to fluorescence detectors, the efforts have focused on solid-state sources such as light-emitting diodes (LEDs) and lasers (VCSELs) [7–10]. However, making these sources for deep UV wavelengths and integrating them with microfluidic systems is a major challenge.

U.S. Pat. No. 6,686,998 discloses a glow discharge apparatus having liquid electrodes including a substrate with a top surface on which cathode and anode electrodes are formed. The cathode electrode may be formed with a cathode terminal port formed to hold a liquid which is spaced from the anode electrode by an inter-electrode surface of the substrate. Electrical conductors are connected to the anode and cathode electrodes to allow a voltage to be applied between them, resulting in a glow discharge in the gap over the inter-electrode surface that causes sputtering of the liquid in the cathode terminal port into the glow discharge. Excitation by the glow discharge of the sputtered or evaporated liquid allows spectroscopic analysis of the constituents of the liquid in the electrode. The glow discharge apparatus utilizes liquid electrodes which allow spectrometric analysis of liquid samples and particularly water samples for determining contaminants in the water. The apparatus may also be utilized as a micro light source that provides light output at visible or non-visible wavelengths that can be selected by selection of the liquid utilized in the electrodes of the materials dissolved or suspended in the electrode liquids. The device to be utilized for on-chip UV sources. Other constituents of the water in the cathode reservoir can be chosen to obtain emission at other wavelengths, including visible wavelengths.

SUMMARY OF THE INVENTION

An object of the present invention is to provide an improved micro-discharge optical source apparatus and an improved method and system for analyzing a sample.

In carrying out the above object and other objects of the present invention, a micro-discharge optical source apparatus is provided. The apparatus includes a substrate and an anode electrode and a cathode electrode supported on the substrate. The electrodes are spaced apart to define an inter-electrode gap therebetween. The apparatus further includes a voltage source for applying a voltage between the electrodes sufficient to generate a glow micro-discharge in the gap to cause a first emission having a first desired excitation spectrum. An optical element is integrated with the substrate to direct the first emission to travel along a first optical path including a first axis.

At least one of the electrodes may be a liquid electrode.

A micro-discharge may excite a first liquid of the liquid electrode to provide the first emission.

The excitation spectrum may include at least one undesired wavelength, and the optical element may attenuate the at least one undesired wavelength.

The optical element may include an optical filter supported along the first optical path to attenuate the at least one undesired wavelength.

The electrodes may be housed within the substrate.

The desired excitation spectrum may include an ultraviolet range.

The substrate may include outer layers and at least one inner layer sandwiched between the outer layers.

The substrate may be a laminate.

At least one of the electrodes may be made of a material to provide the first emission, and the first desired excitation spectrum may include at least one desired wavelength.

The liquid of the liquid electrode may be doped with a compound to tune the first desired excitation spectrum.

The apparatus may further include means for replenishing the liquid electrode with the first liquid.

The apparatus may further include means for changing the liquid of the liquid electrode from the first liquid to a second liquid. The voltage applied by the voltage source may be sufficient to generate a second glow micro-discharge in the gap and to excite the second liquid to provide a second emission having a second desired excitation spectrum.

The apparatus may further include at least one channel formed in the substrate in fluid communication with the liquid electrode to convey the first liquid to the liquid electrode.

The apparatus may further include at least one valve supported on the substrate to control flow of the first liquid from the at least one channel to the liquid electrode.

A plurality of channels may be formed in the substrate to convey at least the first liquid to the liquid electrode and a plurality of valves may be supported on the substrate to control the flow of the at least first liquid from the plurality of channels to the liquid electrode.

The apparatus may further include a lens disposed along the optical path to optically process the first emission.

The voltage may include a pulsed electrical signal sufficient to generate the glow micro-discharge in the gap.

The electrical signal may be variable so that the first desired excitation spectrum is observable for an adjustable delay and time.

The optical element may be disposed along the first optical path.

The optical element may include an optical window, or may include an optical filter.

The gap may be encapsulated sufficiently to substantially prevent contamination of the gap.

The electrodes may be spaced apart in a horizontal direction.

The lens may be a microfluidic lens.

The electrodes may be spaced apart in a vertical direction.

The apparatus may further include at least one microfluidic channel in fluid communication with the liquid electrode and a barrier to prevent migration of chemical species into the at least one microfluidic channel.

The gap may be encapsulated in vacuum with a gas at a predetermined pressure to provide the first desired emission.

The voltage source may include a battery.

The voltage may be sufficient to sputter the first liquid from the liquid electrode into the micro-discharge.

Further in carrying out the above object and other objects of the present invention, a method for analyzing a sample is provided. The method includes providing a substrate and an anode electrode and a cathode electrode supported on the substrate. The electrodes may be spaced apart to define an inter-electrode gap therebetween. A sample reservoir is provided for receiving and retaining a liquid sample at a desired site. The desired site may be optically coupled to the gap. The liquid sample is dispensed in the sample reservoir, and a voltage is applied between the electrodes sufficient to generate a glow micro-discharge in the gap to cause a first emission having a first desired excitation spectrum along a first optical path including a first axis which excites the sample so that the sample provides a second emission having an emission spectrum along a second optical path including a second axis.

At least one of the electrodes may be a liquid electrode.

The micro-discharge may excite a first liquid of the liquid electrode to provide the first emission.

The first desired excitation spectrum may include at least one undesired wavelength. The method may further include attenuating the at least one undesired wavelength.

The method may further include providing an optical filter disposed between the gap and the sample reservoir along the first optical path to attenuate the at least one undesired wavelength.

The method may further include attenuating at least one undesired wavelength of radiant energy along the second optical path.

The method may further include detecting the second emission along the second optical path.

The electrodes may be housed within the substrate.

The sample may include a dye-labeled biochemical.

The sample reservoir may be housed within the substrate.

The sample may further include a biochemical, a fluorophore, or an amino acid.

The first desired excitation spectrum may include an ultraviolet range required to excite the sample.

The substrate may include outer layers and at least one inner layer sandwiched between the outer layers.

The substrate may be a laminate.

The axes may be substantially orthogonal to one another.

The method may further include providing an optical element to optically couple the desired site to the gap.

At least one of the electrodes may be made of a material to provide the first emission. The first desired excitation spectrum may include at least one desired wavelength to excite the sample.

The liquid of the liquid electrode may be doped with a compound to tune the first desired excitation spectrum.

The method may further include replenishing the liquid electrode with the first liquid.

The method may further include changing the liquid of the liquid electrode from the first liquid to a second liquid and applying a voltage between the electrodes sufficient to generate a second glow micro-discharge in the gap and to excite the second liquid to provide a second emission having a second desired excitation spectrum.

The method may further include providing at least one channel in the substrate in fluid communication with the liquid electrode to convey liquid to the liquid electrode.

The method may further include providing at least one valve supported on the substrate to control flow of liquid from the at least one channel to the liquid electrode.

A plurality of channels may be provided in the substrate to convey liquid to the liquid electrode and a plurality of valves may be supported on the substrate to control the flow of liquid from the plurality of channels to the liquid electrode.

The method may further include providing a microfluidic lens to optically couple the desired site to the gap.

The voltage may include a pulsed electrical signal sufficient to generate the glow micro-discharge in the gap.

The electrical signal may be variable so that the first desired excitation spectrum is observable for an adjustable delay and time.

The optical element may separate the gap from the sample reservoir.

The optical element may include an optical window, or may include an optical filter.

Both the gap and the sample reservoir may be encapsulated.

The gap and the sample reservoir may be encapsulated sufficiently to prevent cross contamination between the gap and the sample reservoir.

The method may further include providing a lens in at least one of the optical paths.

The lens may be a liquid lens.

The electrodes may be spaced apart in a vertical direction.

The method may further include providing at least one microfluidic channel in fluid communication with the liquid electrode and a barrier to prevent migration of chemical species into the at least one microfluidic channel.

The gap may be encapsulated in vacuum with a gas at a predetermined pressure to provide the first desired emission.

The electrodes may be spaced apart in a horizontal direction.

The sample reservoir may be a component within another diagnostic or microfluidic system.

Still further in carrying out the above object and other objects of the present invention, a system is provided for analyzing a sample. The system includes a substrate, and an anode electrode and a cathode electrode supported on the substrate. The electrodes are spaced apart to define an inter-electrode gap therebetween. The system further includes a sample reservoir for receiving and retaining a liquid sample at a desired site. The desired site is optically coupled to the gap. The system still further includes a voltage source for applying a voltage between the electrodes sufficient to generate a glow micro-discharge in the gap to cause a first emission having a first desired excitation spectrum along a first optical path including a first axis which excites the sample so that the sample provides a second emission having an emission spectrum along a second optical path including a second axis.

At least one of the electrodes may be a liquid electrode.

The micro-discharge may excite a first liquid of the liquid electrode to provide the first emission.

The first desired excitation spectrum may include at least one undesired wavelength. The system further include an optical element for attenuating the at least one undesired wavelength.

The system may further include an optical filter disposed between the gap and the sample reservoir along the first optical path to attenuate the at least one undesired wavelength.

The system may further include an optical element for attenuating at least one undesired wavelength of radiant energy along the second optical path.

The system may further include a detector for detecting the second emission along the second optical path.

The system may further include a detector for detecting the second emission along the second optical path.

The electrodes may be housed within the substrate.

The sample may include a dye-labeled biochemical.

The sample reservoir may be housed within the substrate.

The sample may include a biochemical, a fluorophore, or an amino acid.

The first desired excitation spectrum may include an ultraviolet range required to excite the sample.

The substrate may include outer layers and at least one inner layer sandwiched between the outer layers.

The substrate may be a laminate.

The axes may be substantially orthogonal to one another.

The system may further include an optical element optically coupling the desired site to the gap.

At least one of the electrodes may be made of a material to provide the first emission, and the first desired excitation spectrum may include at least one desired wavelength to excite the sample.

The liquid of the liquid electrode may be doped with a compound to tune the first desired excitation spectrum.

The system may further include means for replenishing the liquid electrode with the first liquid.

The system may further include means for changing the liquid of the liquid electrode from the first liquid to a second liquid. The voltage applied by the voltage source may be sufficient to generate a second glow micro-discharge in the gap and to excite the second liquid to provide a second emission having a second desired excitation spectrum.

The system may further include at least one channel formed in the substrate in fluid communication with the liquid electrode to convey the first liquid to the liquid electrode.

The system may further include at least one valve supported on the substrate to control the flow of the first liquid from the at least one channel to the liquid electrode.

A plurality of channels may be formed in the substrate to convey at least the first liquid to the liquid electrode and a plurality of valves supported on the substrate to control the flow of the at least first liquid from the plurality of channels to the liquid electrode.

The system may further include a microfluidic lens to optically couple the desired site to the gap.

The voltage may include a pulsed electrical signal sufficient to generate the glow micro-discharge in the gap.

The electrical signal may be variable so that the first desired excitation spectrum is observable for an adjustable delay and time.

The optical element may separate the gap from the sample reservoir.

The optical element may include an optical window, or may include an optical filter.

Both the gap and the sample reservoir may be encapsulated.

The gap and the sample reservoir may be encapsulated sufficiently to prevent cross contamination between the gap and the sample reservoir.

The system may further include a lens disposed in at least one of the optical paths.

The lens may be a liquid lens.

The electrodes may be spaced-apart in a vertical direction.

The system may further include at least one microfluidic channel in fluid communication with the liquid electrode and a barrier to prevent migration of chemical species into the at least one microfluidic channel.

The gap may be encapsulated in vacuum with a gas at a predetermined pressure to provide the first desired emission.

The voltage source may include a battery.

The sample reservoir may be a component within another diagnostic or microfluidic system.

The above object and other objects, features, and advantages of the present invention are readily apparent from the following detailed description of the best mode for carrying out the invention when taken in connection with the accompanying drawings.

DETAILED DESCRIPTION OF THE PREFERRED EMBODIMENTS

In general, what is disclosed herein are micro-discharge optical source apparatus and methods and systems for analyzing a sample. What is described herein is an approach which not only provides a source of illumination with desired wavelengths, but can be easily integrated with micro-total analysis systems because it is preferably a microfluidic device.

Device Structure and Calibration

Figure 2:
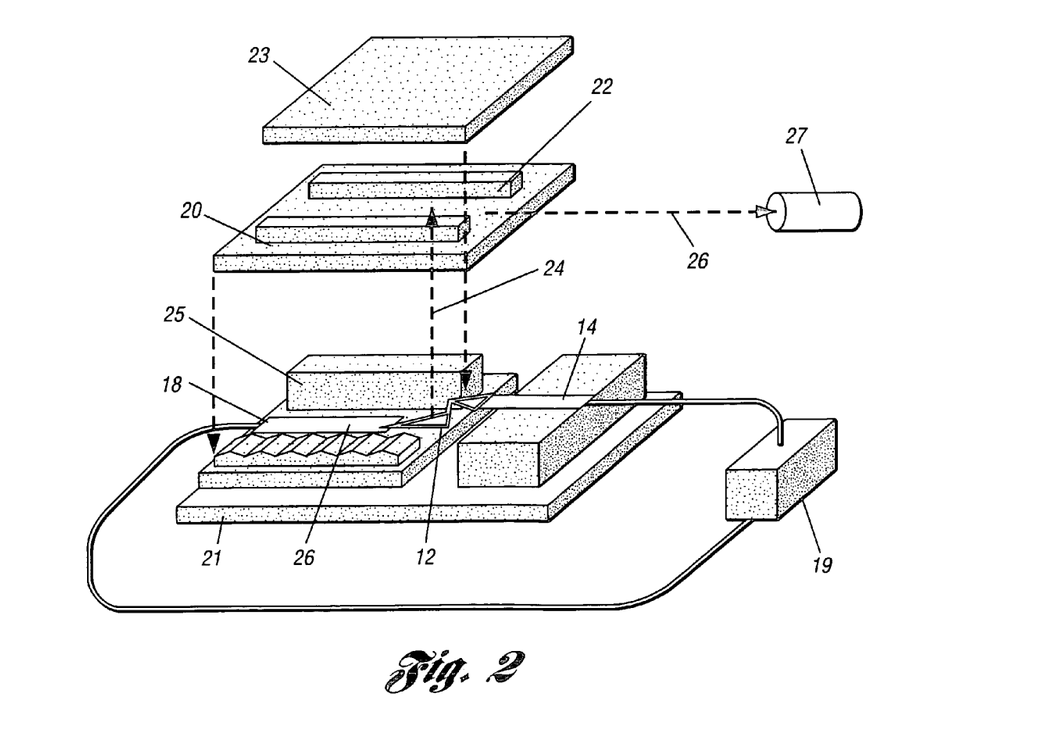
FIG. 2 is an exploded schematic view of a device of one embodiment of the present invention showing various components; the tryptophan sample reservoir can be replaced by a micro-total analysis chip.

The device or apparatus structure is illustrated in FIG. 2. An electrical micro-discharge 12 is ignited across an air gap between a metal anode 14 and a liquid reservoir 16 containing a saturated solution of $Pb(NO_3)_2$ which serves as the cathode 18. A power supply is indicated at 19 and a base is indicated at 21. The micro-discharge 12 sputters the solution from the cathode 18 into its glow region. Atomic transitions in Pb atoms provide the wavelengths necessary to excite amino acids. Unwanted wavelengths are rejected by an optical filter 20 that separates the micro-discharge 12 from the tryptophan sample. The tryptophan is located in a reservoir 22 or channel as part of a micro-total analysis system. A reservoir cover is indicated at 23 and a microchannel wall and spacer is indicated at 25. The overall footprint of the device may be approximately 1 cm×1 cm, with the reservoirs 16 and 22 covering half the area. The assembly may be held horizontally or vertically during operation.

The filtered emission from the discharge pulse follows optical path I 24 (FIG. 2), and stimulates fluorescence in the sample reservoir 22, which emission light is detected along optical path II 26. These paths 24 and 26 are preferably orthogonal to minimize the signal feed-through from the arc to the detector, which may be an Ocean Optics USB 2000™ spectrometer that connects to the USB port of a computer. An optical fiber is indicated at 27.

The overall architecture of this device is based on a fluidic microchip that has been reported for detecting inorganic contamination in water samples [11, and U.S. Pat. No. 6,686,998], and on another device (using $BaCl_2$) for optical fluorescence of biochemicals in the visible regime [12, and as described in greater detail herein below]. However, working with UV wavelengths adds many unique challenges. One should not only find an appropriate liquid source that is easily available for widespread usage, but also develop means to accommodate the relatively weak emission strengths in the 250–290 nm range, and the relatively poor quantum efficiencies of the amino acids. The emission reservoir may be sealed from the amino acid because $Pb^{2+}$ and a number of other metal ions are known to quench fluorescence in tryptophan [4]. Additional constraints are placed on the structural materials with respect to the transmission of these wavelengths.

Figure 3:
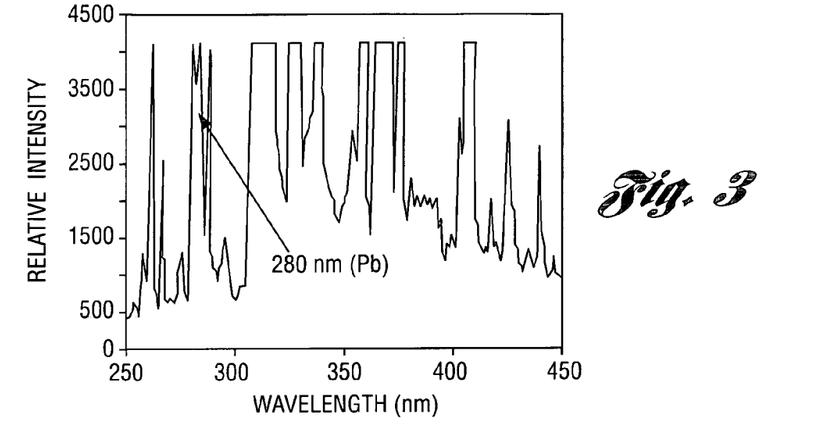
FIG. 3 is a graph of measured spectrum from lean nitrate with concentration of 5 g/10 ml water (saturated solution), showing substantial emission intensity in the 250–290 nm wavelengths.
Figure 4A:
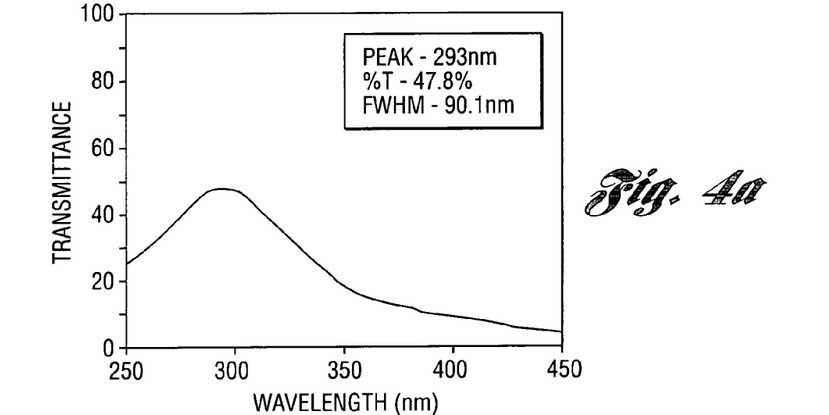
FIG. 4a is a transmission curve of the filter separating the UV source from the tryptophan sample.
Figure 4B:
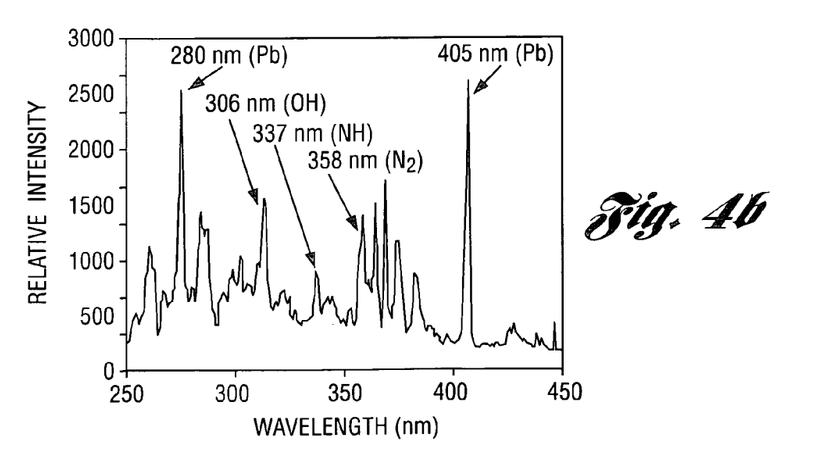
FIG. 4b is a graph of the measured spectrum of the filtered emission, showing increased prominence of 250–290 nm wavelengths as compared to the unfiltered emission in FIG. 3.

The spectral emission obtained by a micro-discharge to the saturated $Pb(NO_3)_2$ solution is shown in FIG. 3. There is a substantial peak near 280 nm, which is characteristic of Pb, and closely matches the excitation peak for tryptophan, as shown in FIG. 1. However, there are also a number of other peaks with high relative strength, which should be suppressed to reduce the likelihood of signal feed-through to the detector. As shown in FIG. 2, this is done by using a filter 20 separate the discharge source from the amino acid. In the present version of the device, a VU-grade filter with a fused silica substrate (#300-W-ID from Acton Research Corp., Acton, Mass.) is used. It has peak transmission wavelength of 293.0 nm and its FWHM is 90.1 nm, with a peak transmittance of 47.8%. The transmission characteristics of the filter and the resulting spectrum that is used to excite the tryptophan are shown in FIG. 4. The undesired wavelengths from the lead nitrate are substantially attenuated. The remaining large peaks (such as those near 368 nm and 405 nm) can be cancelled by a simple calibration in which the spectrum of a control sample of water is subtracted from the spectrum of the tryptophan dissolved in water, as will be demonstrated in the next section.

Experimental Results

A number of measurements were performed using commercially available tryptophan, which was dissolved in DI water at room temperature to prepare a saturated solution [13]. In all the measurements presented, the background radiation in the room was measured immediately before each experiment and subtracted out of the results.

Figure 5A:
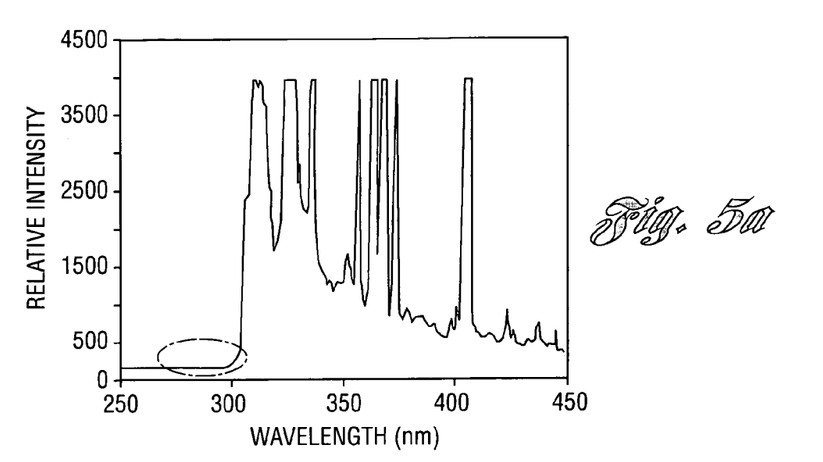
FIG. 5a is a graph of light transmitted through tryptophan which shows that the peaks near 280 nm have been absorbed.
Figure 5B:
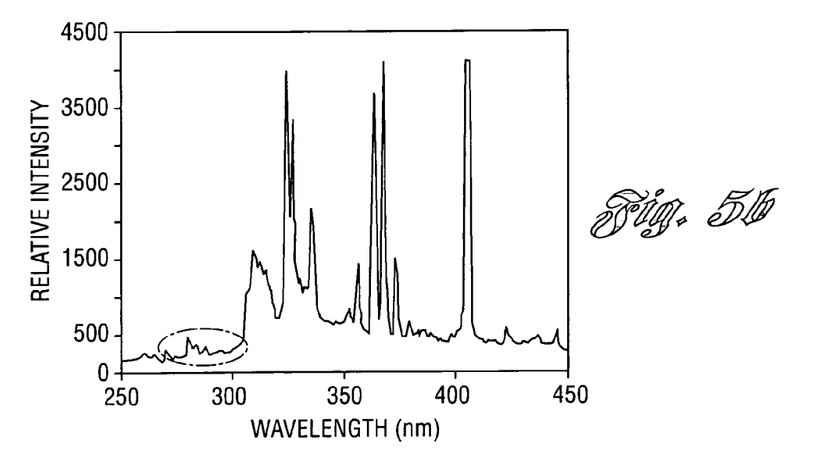
FIG. 5b is a graph which shows wavelengths that are transmitted through the control sample of water.

The absorption of the UV light was studied by placing the optical fiber 27 the same axis as the incident light source (i.e., along optical path I 24). FIG. 5a shows the light spectrum after it passes through a 2.5 mm deep sample of tryptophan solution. Comparing with the excitation spectrum, one can see that tryptophan absorbs the lines in the 280 nm range. To verify this result, a control experiment was done by placing water instead of tryptophan in the sample chamber. FIG. 5b shows that the 280 nm lines pass through the water and can be clearly seen in the transmitted spectrum. This confirms that the tryptophan sample absorbs them. Also, the similarity of the remainder of these two spectra suggests that other attenuation is due to water.

Figure 6:
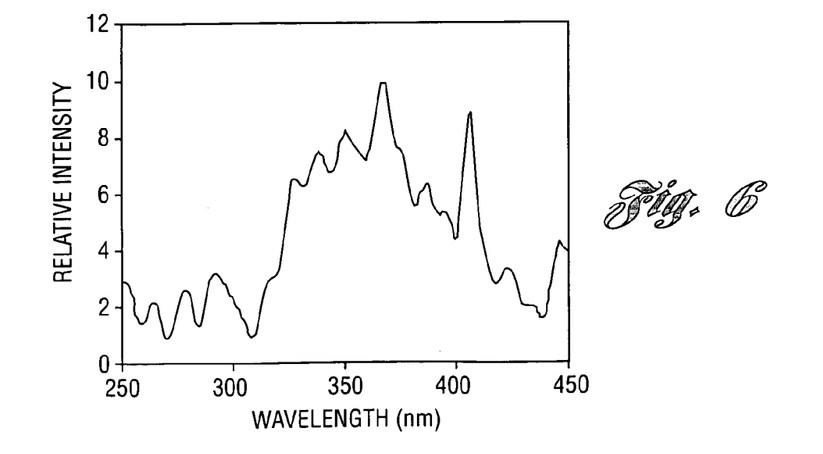
FIG. 6 is a graph of optical emission measured along optical path II (as shown in FIG. 2) indicating the existence of the direct fluorescence of tryptophan by the broad peak between 325 nm and 425 nm.

The fluorescence spectrum was observed by placing the fiber 27 along optical path II 26, transverse to the excitation path to remove the interfering background radiation. FIG. 6 shows the observed output from a tryptophan sample, with evidence of the characteristic broad peak between 300 nm and 450 nm. A control experiment with water in place of tryptophan provides the spectrum shown in FIG. 7 with no evidence of the characteristic broad peak of tryptophan. The peaks near 368 and 405 nm are from spikes of high relative intensity in the lead nitrate spectrum which are not sufficiently attenuated by the filter 20 and are coupled from optical path I 24 to optical path II 26. The curves in FIGS. 6 and 7 were both obtained by integrating the spectrum for 10 seconds and further averaging along the wavelength axis over +15 points from each data point, using a triangular weighting.

Figure 7:
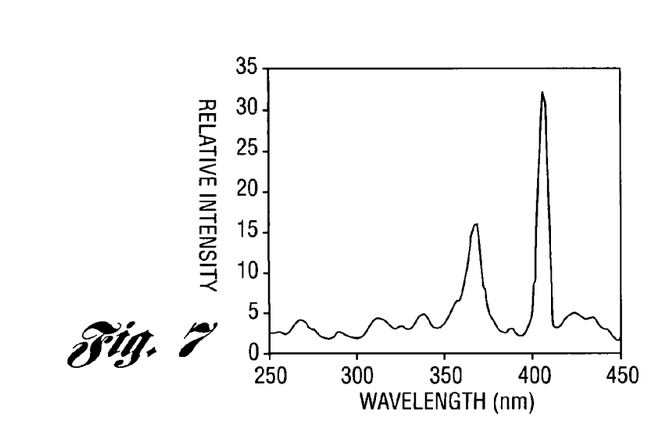
FIG. 7 is a graph of spectrum measured with a DI water control sample in a manner analogous to FIG. 6, and shows the absence of the broad peak between 325 nm and 425 nm.

A simple calibration method in which the spectrum of the water sample is subtracted from that obtained with the tryptophan sample can be used to make the fluorescence emission clearer. However, before doing this, the data in FIGS. 6 and 7 are scaled so that the base-to-peak amplitude at 405 nm are of equal magnitude. It is noteworthy that this calibration at 405 nm also removes the spurious peak at 368 nm.

Figure 8:
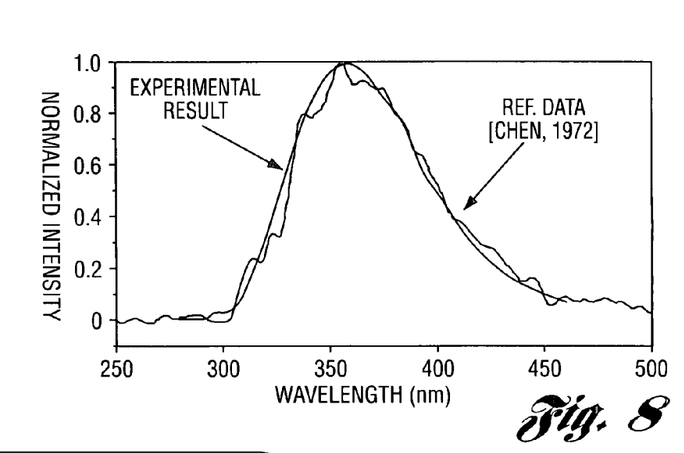
FIG. 8 is a graph showing the net output from the tryptophan sample, obtained by subtracting the curve of FIG. 7 from that of FIG. 6; the reference emission curve of tryptophan [6] has been superimposed.

FIG. 8 shows the observed tryptophan spectrum after the signal processing, superimposed with the reference tryptophan spectrum from [6]. The characteristic broad peak of tryptophan fluorescence is clear. This establishes that the micro-discharge UV source can be used to excite the UV fluorescence.

As described above, it has been experimentally demonstrated that spectral emission from electrical micro-discharges 12 can be used to fluoresce amino acids with excitation wavelengths in the deep UV range. The discharges 12 are generated in air, between a metal anode 14 and a liquid cathode 18, both of which are on-chip. The characteristic fluorescence of tryptophan in a solution of water can be clearly observed using a lead nitrate solution as the source of 280 nm radiation used for the optical excitation of the sample. Since the quantum efficiency of tryptophan fluorescence is about three-fold to four-fold higher in dimethyl sulfoxide (either as free amino acid or when incorporated into a polypeptide chain), it is expected that this method can be used in a variety of tests. Additionally, since the emission stems from characteristic spectra of ions in the liquid cathode, it can be tuned with various species and replenished as needed using a microfluidic system that is disparate from micro-total analysis system that it is serving. Deep UV radiation which is difficult to generate from any other miniature source can be easily generated using simple chemicals in this manner. The microfluidic nature of the emission source also makes it easier to integrate with the micro-total analysis system, and tightly couple the optical emission.

Figure 9A:
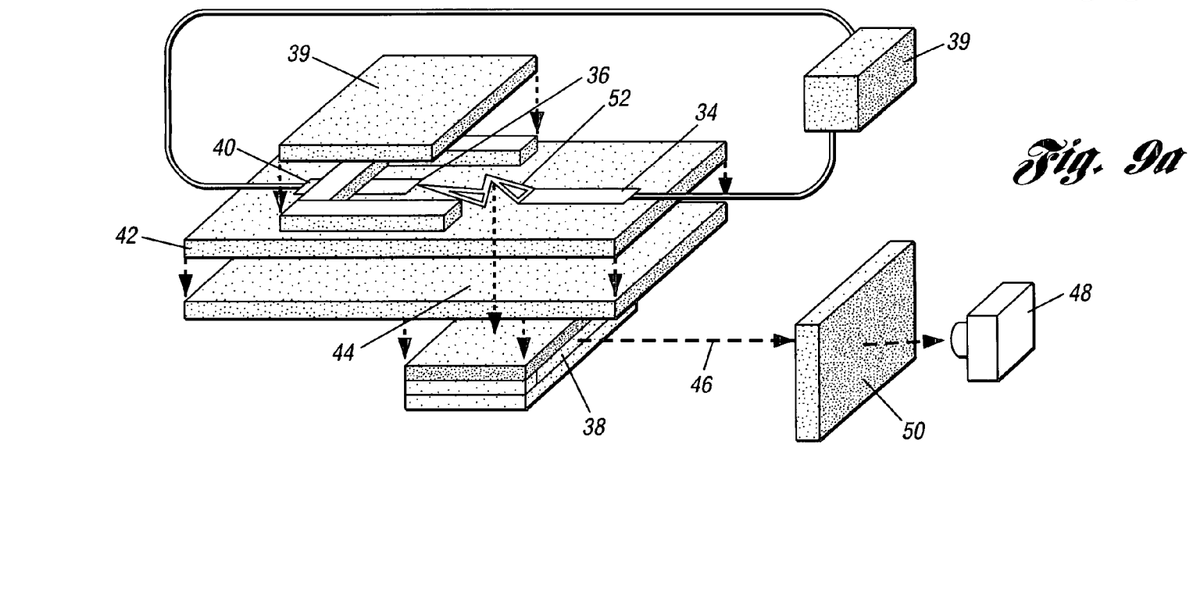
FIG. 9a is an exploded schematic view of the miniaturized device constructed in accordance with a second embodiment of the present invention.

A second embodiment of the present invention involves a dye-fluorescence LEd-SpEC apparatus or device (FIG. 9a), including six glass layers and an integrated optical filter 42. The upper three layers form the micro-discharge source chip, including a metal anode 34 and the liquid cathode reservoir 36, while the bottom three layers form the DNA sample reservoir 38. A reservoir lid is indicated at 39 and a control circuit is indicated at 39. The DNA sample reservoir 38, which is aligned to the optical source, can be part of a larger fluidic system or a disposable plastic chip. The downward-pointing arrows in FIG. 9a indicate how the system is assembled.

Figure 9B:
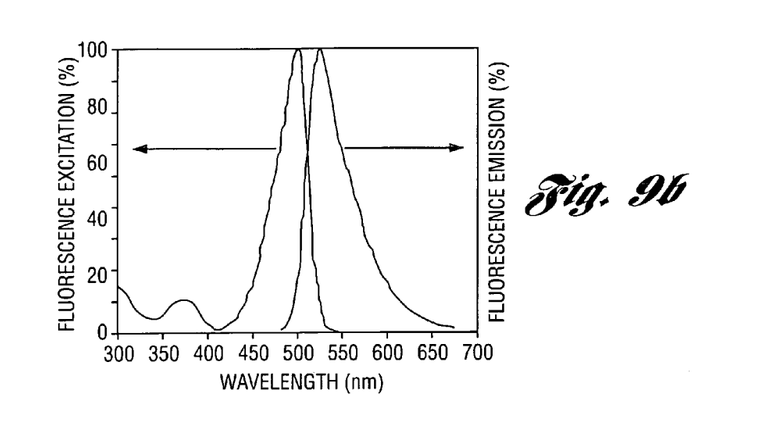
FIG. 9b is a graph which shows how dsDNA-bound SYBR green dye is most efficiently excited near 498 nm; the emission peak is at 522 nm.

The present manifestation of the device is intended for fluorescing SYBR green dye (Molecular Probes, Inc.) tagged to calf thymus dsDNA. The excitation of this dye peaks over 491–503 nm, while emission peaks over 510–600 nm (FIG. 9b). The liquid cathode 40 used is 20% W/V $BaCl_2$. The emission spectrum of Ba provides peaks at 454 and 493 nm, corresponding to 25% and 97% efficiency for this dye, respectively [2]. The proximity of the absorption and emission peaks and the miniature size of the instrument pose a challenge in the optical design of the device. A dichroic bandpass filter 42 (350–500 nm), chosen for its low sensitivity to incident angle and its superior reliability over other types of filters (e.g., interference filter) separates the optical source from the sample reservoir 38 to block unwanted wavelengths [14]. The filtered emission from the discharge pulse follows optical path I 44 (FIG. 9a) and stimulates fluorescence in the biochemical sample reservoir 38, which emmission light is detected along optical path II 46. Paths I and II 44 and 46, respectively, are orthogonal to minimize the possibility of stray light feeding-through from the arc to the detector 48. In addition, a high pass (>500 nm) optical filter 50 placed along path II 46 blocks stray light scattered by the sample from entering the detector 48. All the glass layers are #7740 Pyrex™ glass (506 μm thick) which has transmittance >80% for 300–700 nm wavelengths.

Figure 10A:
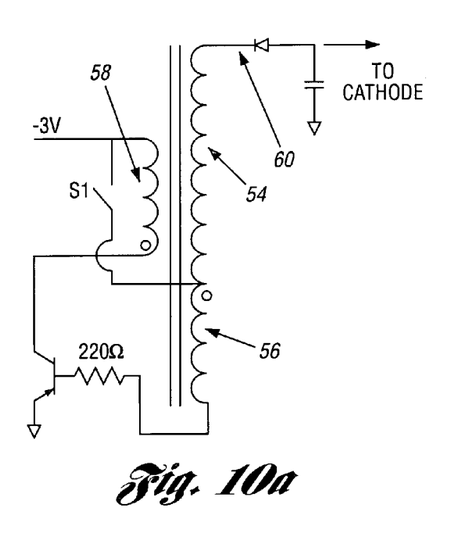
FIG. 10a is a schematic view of a ringing choke converter high voltage circuit.
Figure 10B:
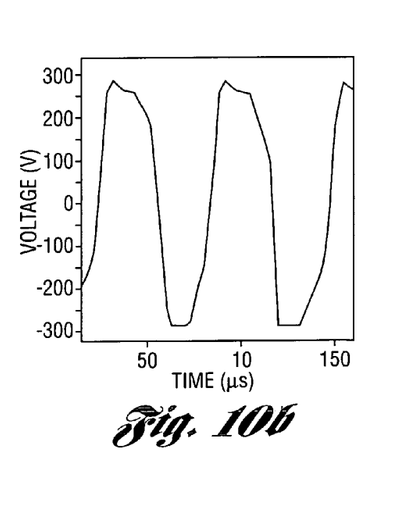
FIG. 10b is a waveform at test point obtained by SPICE simulation of the circuit of FIG. 10a driven by a 1.5 V battery.

The micro-discharge 52 is powered by a pulsed high voltage generated by a 3 V battery-operated circuit (FIG. 10a). The design is based on the ringing choke converter [15], which consists of a transistor-transformer oscillator in which secondary windings 54 on the transformer boost the voltage. When the switch S1 is closed, a small base current starts to flow into the transistor. The rising collector current leads to increasing base current due to positive feedback from the transformer. This drives the transistor into saturation. The rate of change of current then decreases, and the voltage induced in the feedback winding 56 decreases. The base current decreases and transistor turns off. Due to the sudden decrease of collector current, a large voltage drop occurs across the primary winding 58, and consequently on the secondary winding 54. FIG. 10b shows the SPICE simulated waveform at this test point 60 (for which the circuit is driven by a 1.5 V battery). This high voltage AC waveform is rectified and used to charge up the capacitor, which powers the cathode for the pulsed discharge.

Integrating focusing optics such as microfluid lenses between the micro-discharge and the sample optimizes the above optical coupling.

The above microfluidic chip with an integrated micro-discharge source can be used to locally fluoresce biochemicals. The microfluidic nature of the source makes it low cost and amenable for integration with diagnostic systems. Fluorescence of SYBR dye-tagged calf thymus DNA is demonstrated using $BaCl_2$ solution as the cathode 40. This device can be tuned to a variety of wavelengths by the appropriate selection of chemicals.

As described above, fluorescence detection is one of the most widely used techniques for biochemical analysis. For example, DNA strands can be "tagged" with fluorescent dyes that are intercalated into the double-helix, permitting them to be detected by the presence of a characteristic optical emission under illumination by characteristic excitation wavelengths, which are shorter (and hence more energetic). Proteins can be fluorescent even without the presence of a dye, and changes in this intrinsic or direct fluorescence can be indicative of structural transformations.

In recent years, significant research has been devoted to miniaturization of biochemical instrumentation, leading to the development of micro-total analysis systems (also referred to as "lab-on-a-chip") which are essentially microfluidic systems. With respect to fluorescence detectors, the efforts have focused on solid-state sources such as light-emitting diodes and solid-state lasers. However, these sources are not made with the same fabrication techniques common to microfluidic systems. In addition, direct fluorescence of some proteins such as tryptophan require ultraviolet light, which is not readily generated with these sources.

A new approach to producing the illumination which circumvents these challenges is provided herein. A pulsed discharge 52 is ignited between a metal anode 34 and a microfluidic cathode 40 filled with an aqueous solution of a suitable salt. Characteristic transitions of the cat-ions, which are sputtered into the glow region, provide strong emissions at visible and ultraviolet wavelengths. Undesirable wavelengths are blocked out by integrated optical filters 42. Exemplary microstructures, chemicals, and circuits are described for the fluorescence of DNA tagged with dye as well as the direct fluorescence of tryptophan.

The present invention may have one or more of the following features:

An optical source, made by applying high voltage between a metal anode (14, 34, or 64 (i.e., FIG. 11)) and a liquid cathode (18, 40 or 66 (i.e., FIG. 11)) on an insulating substrate:
  whose wavelength can be tuned by doping the liquid cathode (18, 40 or 56) with different compounds;
  which is replenishable by adding more liquid;
  whose output wavelength can be dynamically changeable during experiment by changing the liquid;
  can have multiplicity of fluid channels (see 68, FIG. 11); a valve is indicated at 67;
  is further integratable with micrototal analysis system, for example, in combination with liquid microfluidic lenses; and
  a pulsed electrical signal is applied.

Figure 11:
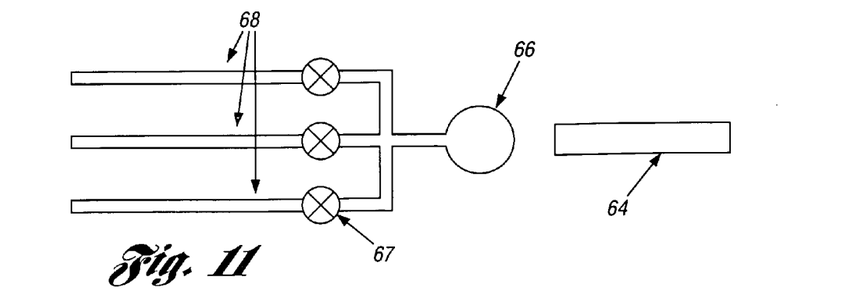
FIG. 11 is a schematic view of a liquid cathode and a metal anode wherein multiple fluid channels and valves control the flow of liquid to and from the liquid cathode.

In the context of pulsed discharge able to adjust the delay and time for which spectra is observed:
  further comprising an integrated optical filter (20 or 42); application to fluorescent imaging by having the analyte in a separate chamber separated by an optical widow/filter;
  with orthogonality of illumination and detection axes in context of fluorescence detection;
  with encapsulation of chambers;
  prevention of cross contamination;
  further comprising liquid/other lenses in either optical path;
  with vertical positioning of electrodes, the anode (14, 34 or 64) on top and cathode (18, 40 or 66) on the bottom;
  with the potential use of a barrier to prevent migration of chemical species into microfluidic channels;
  wherein the cathode (18, 40 or 66) is made of a metal tailored to give light with the required wavelength; and
  where the device is encapsulated in vacuum with a specifically tailored gas at a predetermined pressure.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:
1. A micro-discharge optical source apparatus comprising:
  a substrate;
  an anode electrode and a cathode electrode supported on the substrate wherein the electrodes are spaced apart to define an inter-electrode gap therebetween;

a voltage source for applying a voltage between the electrodes sufficient to generate a glow micro-discharge in the gap to cause a first emission having a first desired excitation spectrum; and an optical element integrated with the substrate to direct the first emission to travel along a first optical path including a first axis.

2. The apparatus as claimed in claim 1, wherein at least one of the electrodes is a liquid electrode and wherein the micro-discharge excites a first liquid of the liquid electrode to provide the first emission.

3. The apparatus as claimed in claim 1, wherein the excitation spectrum includes at least one undesired wavelength and wherein the optical element attenuates the at least one undesired wavelength.

4. The apparatus as claimed in claim 3, wherein the optical element includes an optical filter supported along the first optical path to attenuate the at least one undesired wavelength.

5. The apparatus as claimed in claim 1, wherein the electrodes are housed within the substrate.

6. The apparatus as claimed in claim 1, wherein the desired excitation spectrum includes an ultraviolet range.

7. The apparatus as claimed in claim 1, wherein the substrate includes outer layers and at least one inner layer sandwiched between the outer layers.

8. The apparatus as claimed in claim 1, wherein the substrate is a laminate.

9. The apparatus as claimed in claim 1, wherein at least one of the electrodes is made of a material to provide the first emission and wherein the first desired excitation spectrum includes at least one desired wavelength.

10. The apparatus as claimed in claim 2, wherein the liquid of the liquid electrode is doped with a compound to tune the first desired excitation spectrum.

11. The apparatus as claimed in claim 2, further comprising means for replenishing the liquid electrode with the first liquid.

12. The apparatus as claimed in claim 2, further comprising means for changing the liquid of the liquid electrode from the first liquid to a second liquid wherein the voltage applied by the voltage source is sufficient to generate a second glow micro-discharge in the gap and to excite the second liquid to provide a second emission having a second desired excitation spectrum.

13. The apparatus as claimed in claim 2, further comprising at least one channel formed in the substrate in fluid communication with the liquid electrode to convey the first liquid to the liquid electrode.

14. The apparatus as claimed in claim 13, further comprising at least one valve supported on the substrate to control flow of the first liquid from the at least one channel to the liquid electrode.

15. The apparatus as claimed in claim 14, wherein a plurality of channels are formed in the substrate to convey at least the first liquid to the liquid electrode and a plurality of valves are supported on the substrate to control the flow of the at least first liquid from the plurality of channels to the liquid electrode.

16. The apparatus as claimed in claim 1, wherein the voltage includes a pulsed electrical signal sufficient to generate the glow micro-discharge in the gap.

17. The apparatus as claimed in claim 16, wherein the electrical signal is variable so that the first desired excitation spectrum is observable for an adjustable delay and time.

18. The apparatus as claimed in claim 1, wherein the optical element is disposed along the first optical path.

19. The apparatus as claimed in claim 18, wherein the optical element includes an optical filter.

20. The apparatus as claimed in claim 1, wherein the gap is encapsulated.

21. The apparatus as claimed in claim 20, wherein the gap is encapsulated sufficiently to substantially prevent contamination of the gap.

22. The apparatus as claimed in claim 1, wherein the electrodes are spaced apart in a horizontal direction.

23. The apparatus as claimed in claim 2, further comprising at least one microfluidic channel in fluid communication with the liquid electrode and a barrier to prevent migration of chemical species into the at least one microfluidic channel.

24. The apparatus as claimed in claim 1, wherein the gap is encapsulated in vacuum with a gas at a predetermined pressure to provide the first desired emission.

25. The apparatus as claimed in claim 1, wherein the voltage source includes a battery.

26. The apparatus as claimed in claim 2, wherein the voltage is sufficient to sputter the first liquid from the liquid electrode into the micro-discharge.

27. A method for analyzing a sample, the method comprising:

providing a substrate and an anode electrode and a cathode electrode supported on the substrate wherein the electrodes are spaced apart to define an inter-electrode gap therebetween;

providing a sample reservoir for receiving and retaining a liquid sample at a desired site wherein the desired site is optically coupled to the gap;

dispensing the liquid sample in the sample reservoir; and applying a voltage between the electrodes sufficient to generate a glow micro-discharge in the gap to cause a first emission having a first desired excitation spectrum along a first optical path including a first axis which excites the sample so that the sample provides a second emission having an emission spectrum along a second optical path including a second axis.

28. The method as claimed in claim 27, wherein at least one of the electrodes is a liquid electrode and wherein the micro-discharge excites a first liquid of the liquid electrode to provide the first emission.

29. A method as claimed in claim 27, wherein the first desired excitation spectrum includes at least one undesired wavelength and wherein the method further comprises attenuating the at least one undesired wavelength.

30. The method as claimed in claim 29, further comprising providing an optical filter disposed between the gap and the sample reservoir along the first optical path to attenuate the at least one undesired wavelength.

31. The method as claimed in claim 27, further comprising attenuating at least one undesired wavelength of radiant energy along the second optical path.

32. The method as claimed in claim 27, further comprising detecting the second emission along the second optical path.

33. The method as claimed in claim 31, further comprising detecting the second emission along the second optical path.

34. The method as claimed in claim 27, wherein the electrodes are housed within the substrate.

35. The method as claimed in claim 27, wherein the sample includes a dye-labeled biochemical.

36. The method as claimed in claim 27, wherein the sample reservoir is housed within the substrate.

37. The method as claimed in claim 27, wherein the sample includes a biochemical.

38. The method as claimed in claim 27, wherein the sample includes a fluorophore.

39. The method as claimed in claim 27, wherein the sample includes an amino acid.

40. The method as claimed in claim 27, wherein the first desired excitation spectrum includes an ultraviolet range required to excite the sample.

41. The method as claimed in claim 27, wherein the substrate includes outer layers and at least one inner layer sandwiched between the outer layers.

42. The method as claimed in claim 27, wherein the substrate is a laminate.

43. The method as claimed in claim 27, wherein the axes are substantially orthogonal to one another.

44. The method as claimed in claim 27, further comprising providing an optical element to optically couple the desired site to the gap.

45. The method as claimed in claim 27, wherein at least one of the electrodes is made of a material to provide the first emission and wherein the first desired excitation spectrum includes at least one desired wavelength to excite the sample.

46. The method as claimed in claim 28, wherein the liquid of the liquid electrode is doped with a compound to tune the first desired excitation spectrum.

47. The method as claimed in claim 28, further comprising replenishing the liquid electrode with the first liquid.

48. The method as claimed in claim 28, further comprising changing the liquid of the liquid electrode from the first liquid to a second liquid and applying a voltage between the electrodes sufficient to generate a second glow micro-discharge in the gap and to excite the second liquid to provide a second emission having a second desired excitation spectrum.

49. The method as claimed in claim 28, further comprising providing at least one channel in the substrate in fluid communication with the liquid electrode to convey liquid to the liquid electrode.

50. The method as claimed in claim 49, further comprising providing at least one valve supported on the substrate to control flow of liquid from the at least one channel to the liquid electrode.

51. The method as claimed in claim 50, wherein a plurality of channels are provided in the substrate to convey liquid to the liquid electrode and a plurality of valves are supported on the substrate to control the flow of liquid from the plurality of channels to the liquid electrode.

52. The method as claimed in claim 27, further comprising providing a microfluidic lens to optically couple the desired site to the gap.

53. The method as claimed 27, wherein the voltage includes a pulsed electrical signal sufficient to generate the glow micro-discharge in the gap.

54. The method as claimed in claim 53, wherein the electrical signal is variable so that the first desired excitation spectrum is observable for an adjustable delay and time.

55. The method as claimed in claim 44, wherein the optical element separates the gap from the sample reservoir.

56. The method as claimed in claim 55, wherein the optical element includes an optical window.

57. The method as claimed in claim 55, wherein the optical element includes an optical filter.

58. The method as claimed in claim 27, wherein both the gap and the sample reservoir are encapsulated.

59. The method as claimed in claim 58, wherein the gap and the sample reservoir are encapsulated sufficiently to prevent cross contamination between the gap and the sample reservoir.

60. The method as claimed in claim 27, further comprising providing a lens in at least one of the optical paths.

61. The method as claimed in claim 60, wherein the lens is a liquid lens.

62. The method as claimed in claim 27, wherein the electrodes are spaced apart in a vertical direction.

63. The method as claimed in claim 28, further comprising providing at least one microfluidic channel in fluid communication with the liquid electrode and a barrier to prevent migration of chemical species into the at least one microfluidic channel.

64. The method as claimed in claim 27, wherein the gap is encapsulated in vacuum with a gas at a predetermined pressure to provide the first desired emission.

65. The method as claimed in claim 27, wherein the electrodes are spaced apart in a horizontal direction.

66. The method as claimed in claim 27, wherein the sample reservoir is a component within another diagnostic or microfluidic system.

67. A system for analyzing a sample, the system comprising:
a substrate;
an anode electrode and a cathode electrode supported on the substrate wherein the electrodes are spaced apart to define an inter-electrode gap therebetween;
a sample reservoir for receiving and retaining a liquid sample at a desired site wherein the desired site is optically coupled to the gap; and
a voltage source for applying a voltage between the electrodes sufficient to generate a glow micro-discharge in the gap to cause a first emission having a first desired excitation spectrum along a first optical path including a first axis which excites the sample so that the sample provides a second emission having an emission spectrum along a second optical path including a second axis.

68. The system as claimed in claim 67, wherein at least one of the electrodes is a liquid electrode and wherein the micro-discharge excites a first liquid of the liquid electrode to provide the first emission.

69. The system as claimed in claim 67, wherein the first desired excitation spectrum includes at least one undesired wavelength and wherein the system further comprises an optical element for attenuating the at least one undesired wavelength.

70. The system as claimed in claim 69, further comprising an optical filter disposed between the gap and the sample reservoir along the first optical path to attenuate the at least one undesired wavelength.

71. The system as claimed in claim 67, further comprising an optical element for attenuating at least one undesired wavelength of radiant energy along the second optical path.

72. The system as claimed in claim 67, further comprising a detector for detecting the second emission along the second optical path.

73. The system as claimed in claim 71, further comprising a detector for detecting the second emission along the second optical path.

74. The system as claimed in claim 67, wherein the electrodes are housed within the substrate.

75. The system as claimed in claim 67, wherein the sample includes a dye-labeled biochemical.

76. The system as claimed in claim 67, wherein the sample reservoir is housed within the substrate.

77. The system as claimed in claim 67, wherein the sample includes a biochemical.

78. The system as claimed in claim 67, wherein the sample includes a fluorophore.

79. The system as claimed in claim 67, wherein the sample includes an amino acid.

80. The system as claimed in claim 67, wherein the first desired excitation spectrum includes an ultraviolet range required to excite the sample.

81. The system as claimed in claim 67, wherein the substrate includes outer layers and at least one inner layer sandwiched between the outer layers.

82. The system as claimed in claim 67, wherein the substrate is a laminate.

83. The system as claimed in claim 67, wherein the axes are substantially orthogonal to one another.

84. The system as claimed in claim 67, further comprising an optical element optically coupling the desired site to the gap.

85. The system as claimed in claim 67, wherein at least one of the electrodes is made of a material to provide the first emission and wherein the first desired excitation spectrum includes at least one desired wavelength to excite the sample.

86. The system as claimed in claim 68, wherein the liquid of the liquid electrode is doped with a compound to tune the first desired excitation spectrum.

87. The system as claimed in claim 68, further comprising means for replenishing the liquid electrode with the first liquid.

88. The system as claimed in claim 68, further comprising means for changing the liquid of the liquid electrode from the first liquid to a second liquid wherein the voltage applied by the voltage source is sufficient to generate a second glow micro-discharge in the gap and to excite the second liquid to provide a second emission having a second desired excitation spectrum.

89. The system as claimed in claim 68, further comprising at least one channel formed in the substrate in fluid communication with the liquid electrode to convey the first liquid to the liquid electrode.

90. The system as claimed in claim 89, further comprising at least one valve supported on the substrate to control the flow of the first liquid from the at least one channel to the liquid electrode.

91. The system as claimed in claim 90, wherein a plurality of channels are formed in the substrate to convey at least the first liquid to the liquid electrode and a plurality of valves supported on the substrate to control the flow of the at least first liquid from the plurality of channels to the liquid electrode.

92. The system as claimed 67, wherein the voltage includes a pulsed electrical signal sufficient to generate the glow micro-discharge in the gap.

93. The system as claimed in claim 92, wherein the electrical signal is variable so that the first desired excitation spectrum is observable for an adjustable delay and time.

94. The system as claimed in claim 84, wherein the optical element separates the gap from the sample reservoir.

95. The system as claimed in claim 94, wherein the optical element includes an optical filter.

96. The system as claimed in claim 67, wherein both the gap and the sample reservoir are encapsulated.

97. The system as claimed in claim 96, wherein the gap and the sample reservoir are encapsulated sufficiently to prevent cross contamination between the gap and the sample reservoir.

98. The system as claimed in claim 68, further comprising at least one microfluidic channel in fluid communication with the liquid electrode and a barrier to prevent migration of chemical species into the at least one microfluidic channel.

99. The system as claimed in claim 67, wherein the gap is encapsulated in vacuum with a gas at a predetermined pressure to provide the first desired emission.

100. The system as claimed in claim 67, wherein the voltage source includes a battery.

101. The system as claimed in claim 67, wherein the sample reservoir is a component within another diagnostic or microfluidic system.

* * * * *